(12) United States Patent
Morgan et al.

(10) Patent No.: US 9,707,324 B2
(45) Date of Patent: Jul. 18, 2017

(54) CONTAINER, SYSTEM, AND METHOD FOR COLLECTING MEDICAL WASTE

(71) Applicant: THE CLEVELAND CLINIC FOUNDATION, Cleveland, OH (US)

(72) Inventors: Joseph W. Morgan, Cleveland Hts., OH (US); Scott R. Schell, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 77 days.

(21) Appl. No.: 14/681,515

(22) Filed: Apr. 8, 2015

(65) Prior Publication Data

US 2015/0291352 A1    Oct. 15, 2015

Related U.S. Application Data

(60) Provisional application No. 61/977,267, filed on Apr. 9, 2014, provisional application No. 62/046,199, filed on Sep. 5, 2014.

(51) Int. Cl.
*B65F 1/06* (2006.01)
*B65F 1/10* (2006.01)
(Continued)

(52) U.S. Cl.
CPC ........ *A61M 1/0017* (2014.02); *A61M 1/0019* (2013.01)

(58) Field of Classification Search
CPC ...... B65F 1/06; B65F 1/10; B65F 1/14; B65F 1/00; B65F 1/0006; B65F 1/607;
(Continued)

(56) References Cited

U.S. PATENT DOCUMENTS 3,814,098 A * 6/1974 Deaton ............... A61M 1/0001
604/320
5,494,196 A * 2/1996 Tyner ........................ A61J 1/10
215/256
(Continued)

FOREIGN PATENT DOCUMENTS

EP    2256575 B1    2/2012
WO    8810124 A1    12/1988

OTHER PUBLICATIONS

International Search Report and Written Opinion for PCT/US2015/024897, mailed Jul. 15, 2015, pp. 1-9.

*Primary Examiner* — Philip R Wiest
*Assistant Examiner* — Sara Sass
(74) *Attorney, Agent, or Firm* — Tarolli, Sundheim, Covell & Tummino LLP

(57) ABSTRACT

A medical waste container comprises a bag with a flexible body defining a cavity and having a fill opening. A tube has a closed end in the bag and an opposite open end projecting from the bag. An elastic ring attached to the bag around the fill opening presses against the tube. A lip projects from the tube adjacent its closed end. A tab also projects from the tube, and a discharge opening is formed in the tube between the lip and the tab. A flow path extends from the open end of the tube into the cavity when the elastic ring encircles the tube at a first position between the tab and the open end. The ring slips over the tab from the first position to a second position in which the ring covers the discharge opening as liquid passes through the flow path, adding weight to the bag.

8 Claims, 6 Drawing Sheets

(51) Int. Cl.
*B65F 1/14* (2006.01)
*B65F 1/00* (2006.01)
*A61M 1/00* (2006.01)

(58) Field of Classification Search
CPC .............. A61M 1/0017; A61M 1/0019; A61M 1/0021; A61M 1/0023; A61M 1/0049; A61M 1/005
See application file for complete search history.

(56) References Cited

U.S. PATENT DOCUMENTS

| | | | |
|---|---|---|---|
| 6,797,857 B2 | 9/2004 | Tanhehco | |
| 2002/0023678 A1* | 2/2002 | Takahashi | A61M 1/0049 137/433 |
| 2009/0034886 A1* | 2/2009 | Conforti | B65D 33/24 383/43 |
| 2011/0259471 A1 | 10/2011 | Maness | |

* cited by examiner

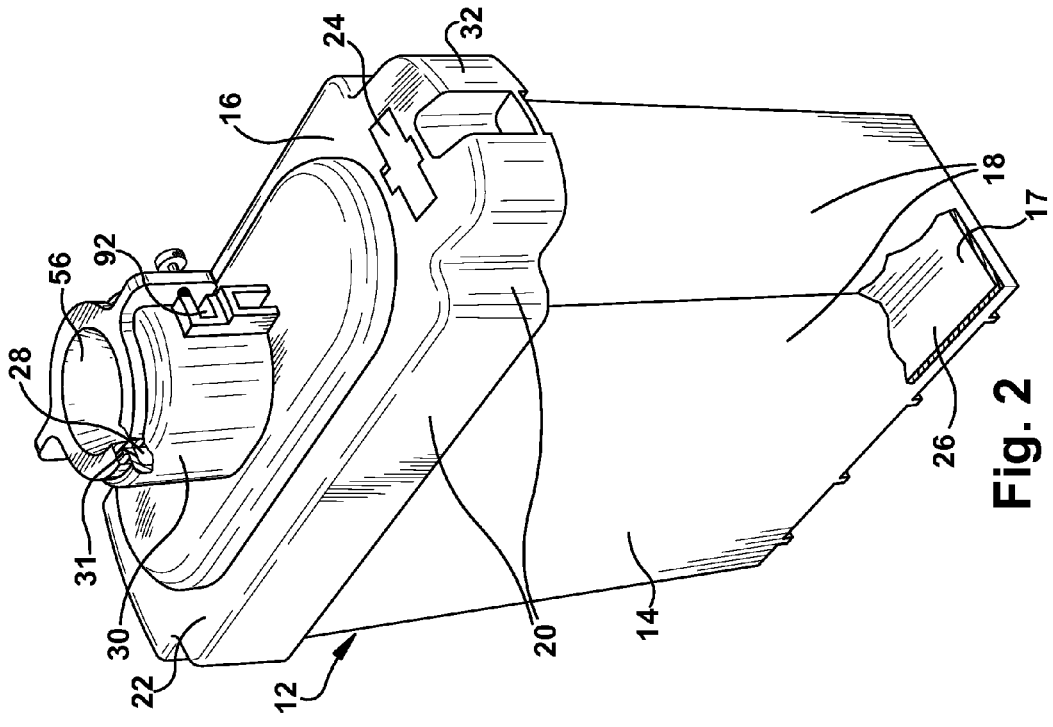
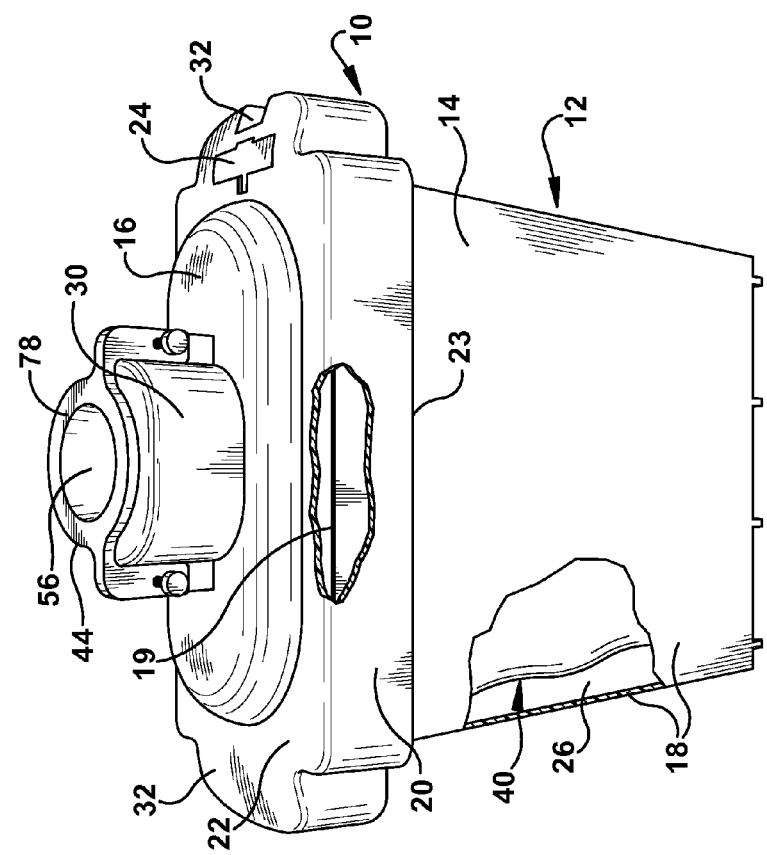

CONTAINER, SYSTEM, AND METHOD FOR COLLECTING MEDICAL WASTE

CROSS-REFERENCE TO RELATED APPLICATIONS

This application claims priority from U.S. Provisional Application Ser. No. 61/977,267, filed Apr. 9, 2014 and U.S. Provisional Application Ser. No. 62/046,199, filed Sep. 5, 2014, the entire contents of which are incorporated herein by reference.

FIELD OF INVENTION

The present invention relates to a container, system, and method for collecting medical waste and, more particularly, to a container and system in which a flexible bag receives a fill tube and to a method of collecting medical waste with such a container and system.

BACKGROUND OF THE INVENTION

Collection and disposal of medical waste requires particular care to avoid environmental contamination and to prevent unauthorized individuals from gaining access to pharmaceutical compounds that may be included in such waste. Systems and devices for such collection and disposal need to be cost effective, convenient to use, and sufficiently secure to prevent unauthorized diversion.

SUMMARY OF THE INVENTION

The present invention is directed to a container, system, and method for collecting medical waste and, more particularly, to a container and system in which a flexible bag receives a fill tube and to a method of collecting medical waste with such a container and system.

In accordance with an embodiment of the present invention, a container for collecting liquid medical waste comprises a bag including a flexible body defining a cavity in the bag. A fill opening is formed in the flexible body. The liquid medical waste container also comprises a fill tube that includes a tubular wall. The fill tube has an open first end and an opposite closed second end. The tubular wall defines a longitudinal passage extending from the first end of the fill tube toward the second end. The second end of the fill tube is receivable in the cavity of the bag with the first end and at least a portion of a length of the tubular wall projecting from the fill opening in the flexible body. The liquid medical waste container further comprises an elastic ring attached to the flexible body adjacent to and surrounding the fill opening. The elastic ring is shaped and dimensioned to encircle and resiliently press against the tubular wall of the fill tube. A lip projects radially outward from the tubular wall adjacent the second end of the fill tube. A tab projects radially outward from the tubular wall at a location spaced apart from the lip in a direction along the tubular wall toward the first end. A discharge opening is formed in the tubular wall of the fill tube between the lip and the tab. The discharge opening extends from an inner surface of the tubular wall to an outer surface of the tubular wall and communicates with the longitudinal passage. A flow path for liquids extends from the open end of the fill tube into the cavity when the fill opening receives the closed end of the fill tube and the elastic ring encircles the fill tube at a first position between the tab and the first end of the fill tube. The flow path is blocked when the elastic ring encircles the fill tube at a second position between the lip and the tab in which the elastic ring covers the discharge opening. The tab is shaped and dimensioned and the elastic ring is formed such that the elastic ring resiliently expands to slip over the tab from the first position to the second position in response to liquid flowing through the flow path into the cavity and adding weight to the bag.

In accordance with another embodiment of the present invention, a method of collecting liquid medical waste comprises the step of inserting a fill tube into a fill opening formed in a flexible body of a bag. The flexible body defines a cavity in the bag. The fill tube has an open first end and an opposite closed second end. The fill tube includes a tubular wall defining a longitudinal passage extending from the first end of the fill tube to the second end. The second end of the fill tube is received in the cavity of the flexible body with the first end and at least a portion of a length of the tubular wall projecting from the fill opening in the flexible body. The method also comprises the step of positioning the fill tube such that an elastic ring attached to the flexible body adjacent to and surrounding the fill opening resiliently presses against the tubular wall of the fill tube at a first position. The first location is disposed between the first end of the fill tube and a tab projecting radially outward from the tubular wall. The method further comprises the step of introducing liquid medical waste into the first end of the fill tube so that the liquid medical waste flows along a flow path extending from the first end of the fill tube through the longitudinal passage and through a discharge opening formed in the tubular wall of the fill tube adjacent the second end of the fill tube. The discharge opening extends from an inner surface of the wall to an outer surface of the wall and communicating with the longitudinal passage. The method still further comprises the step of continuing to introduce liquid medical waste into the first end of the fill tube until liquid flowing through the flow path into the cavity adds sufficient weight to the bag that the elastic ring resiliently expands to slip over the tab from the first position into a second position between the tab and a lip projecting radially outward from the tubular wall adjacent the second end of the fill tube. The elastic ring covers the discharge opening so as to block the flow path when the elastic ring encircles the fill tube at the second position.

In accordance with a further embodiment of the present invention, a container for collecting liquid medical waste comprises a bag including a flexible body defining a cavity in the bag. A fill opening is formed in the flexible body. The liquid medical waste container also comprises a fill tube that includes a tubular wall. The fill tube has an open first end and an opposite closed second end. The tubular wall defines a longitudinal passage extending from the first end of the fill tube toward the second end. The second end of the fill tube is receivable in the cavity of the bag with the first end and at least a portion of a length of the tubular wall projecting from the fill opening in the flexible body. The liquid medical waste container further comprises an elastic ring attached to the flexible body adjacent to and surrounding the fill opening. The elastic ring is shaped and dimensioned to encircle and resiliently press against the tubular wall of the fill tube. A discharge opening is formed in the tubular wall of the fill tube. The discharge opening extends from an inner surface of the tubular wall to an outer surface of the tubular wall and communicates with the longitudinal passage. A flow path for liquids extends from the open end of the fill tube into the cavity when the fill opening receives the closed end of the fill tube and the elastic ring encircles the fill tube at a first position. The flow path is blocked when the elastic ring encircles the fill tube at a second position in which the elastic ring covers the discharge opening. The elastic ring is formed such that the elastic ring moves from the first position to the second position in response to liquid flowing through the flow path into the cavity and adding weight to the bag.

In accordance with still a further embodiment of the present invention, a system for collecting medical waste comprises a solid waste processing assembly. The solid waste processing assembly includes (a) a reducing mechanism operable to reduce solid waste material to a smaller reduced size and (b) a neutralizing mechanism operable to treat the solid waste material with a liquid neutralizing agent to neutralize pharmaceutical products in the solid waste material. The system also comprises a bag including a flexible body defining a cavity in the bag. A fill opening is formed in the flexible body. The system further comprises a fill tube that includes a tubular wall. The fill tube has an open first end and an opposite closed second end. The tubular wall defines a longitudinal passage extending from the first end of the fill tube toward the second end. The second end of the fill tube is receivable in the cavity of the bag with the first end and at least a portion of a length of the tubular wall projecting from the fill opening in the flexible body. The first end of the fill tube is in communication with the solid waste processing assembly. The system still further comprises an elastic ring attached to the flexible body adjacent to and surrounding the fill opening. The elastic ring is shaped and dimensioned to encircle and resiliently press against the tubular wall of the fill tube. A lip projects radially outward from the tubular wall adjacent the second end of the fill tube. A tab projects radially outward from the tubular wall at a location spaced apart from the lip in a direction along the tubular wall toward the first end. A discharge opening is formed in the tubular wall of the fill tube between the lip and the tab. The discharge opening extends from an inner surface of the tubular wall to an outer surface of the tubular wall and communicates with the longitudinal passage. A flow path for liquids and for reduced size solid waste material extends from the open end of the fill tube into the cavity when the fill opening receives the second end of the fill tube and the elastic ring encircles the fill tube at a first position between the tab and the first end of the fill tube. The flow path is blocked when the elastic ring encircles the fill tube at a second position between the lip and the tab covering the discharge opening. The tab is shaped and dimensioned and the elastic ring is formed such that the elastic ring resiliently expands to slip over the tab from the first position to the second position in response to liquid and reduced size solid waste material passing through the flow path into the cavity and adding weight to the bag.

In accordance with yet another embodiment of the present invention, a method of collecting medical waste comprises the step of inserting a fill tube into a fill opening formed in a flexible body of a bag. The flexible body defines a cavity in the bag. The fill tube has an open first end and an opposite closed second end. The fill tube includes a tubular wall defining a longitudinal passage extending from the first end of the fill tube to the second end. The second end of the fill tube is received in the cavity of the flexible body with the first end and at least a portion of a length of the tubular wall projecting from the fill opening in the flexible body. The method also comprises the step of positioning the fill tube such that an elastic ring attached to the flexible body adjacent to and surrounding the fill opening resiliently presses against the tubular wall of the fill tube at a first position. The first position is disposed between the first end of the fill tube and a tab projecting radially outward from the tubular wall. The method further comprises the step of positioning a solid waste processing assembly in communication with the first end of the fill tube. The solid waste processing assembly includes (a) a reducing mechanism operable to reduce solid waste material to a smaller reduced size and (b) a neutralizing mechanism operable to treat the solid waste material with a liquid neutralizing agent to neutralize pharmaceutical products in the solid waste material. The method still further comprises the step of introducing solid medical waste into the solid waste processing assembly and operating the solid waste processing assembly so that reduced size solid medical waste and liquid neutralizing agent pass along a flow path extending from the solid waste processing assembly through the longitudinal passage and through a discharge opening formed in the tubular wall of the fill tube adjacent the second end of the fill tube. The discharge opening extends from an inner surface of the tubular wall to an outer surface of the tubular wall and communicating with the longitudinal passage. The method yet further comprises repeating the step of introducing solid medical waste into the solid waste processing assembly and operating the solid waste processing assembly until reduced size solid medical waste and liquid neutralizing agent passing through the flow path into the cavity adds sufficient weight to the bag that the elastic ring resiliently expands to slip over the tab from the first position into a second position between the tab and a lip projecting radially outward from the tubular wall adjacent the second end of the tubular wall. The elastic ring covers the discharge opening so as to block the flow path when the elastic ring encircles the fill tube at the second position.

In accordance with yet a further embodiment of the present invention, a system for collecting medical waste comprises a solid waste processing assembly. The solid waste processing assembly includes (a) a reducing mechanism operable to reduce solid waste material to a smaller reduced size and (b) a neutralizing mechanism operable to treat the solid waste material with a liquid neutralizing agent to neutralize pharmaceutical products in the solid waste material. The system also comprises a bag that includes a flexible body defining a cavity in the bag. A fill opening is formed in the flexible body. The system further comprises a fill tube that includes a tubular wall. The fill tube has an open first end and an opposite closed second end. The tubular wall defines a longitudinal passage extending from the first end of the fill tube toward the second end. The second end of the fill tube is receivable in the cavity of the bag with the first end and at least a portion of a length of the tubular wall projecting from the fill opening in the flexible body. The first end of the fill tube is in communication with the solid waste processing assembly. The system still further comprises an elastic ring attached to the flexible body adjacent to and surrounding the fill opening. The elastic ring is shaped and dimensioned to encircle and resiliently press against the tubular wall of the fill tube. A discharge opening is formed in the tubular wall of the fill tube. The discharge opening extends from an inner surface of the tubular wall to an outer surface of the tubular wall and communicates with the longitudinal passage. A flow path for liquids and for reduced size solid waste material extends from the open end of the fill tube into the cavity when the fill opening receives the second end of the fill tube and the elastic ring encircles the fill tube at a first position. The flow path is blocked when the elastic ring encircles the fill tube at a second position in which the elastic ring covers the discharge opening. The elastic ring is formed such that the elastic ring moves from the first position to the second position in response to liquid and reduced size solid waste material passing through the flow path into the cavity and adding weight to the bag.

BRIEF DESCRIPTION OF THE DRAWINGS

The foregoing and other features and advantages of the present invention will become apparent to those skilled in the art to which the present invention relates upon reading the following description with reference to the accompanying drawings, in which:

FIG. 1 is a perspective view of a container system for liquid medical waste in accordance with an embodiment of the present invention;

FIG. 2 is a perspective view of the container system of FIG. 1;

DETAILED DESCRIPTION

Figure 3:
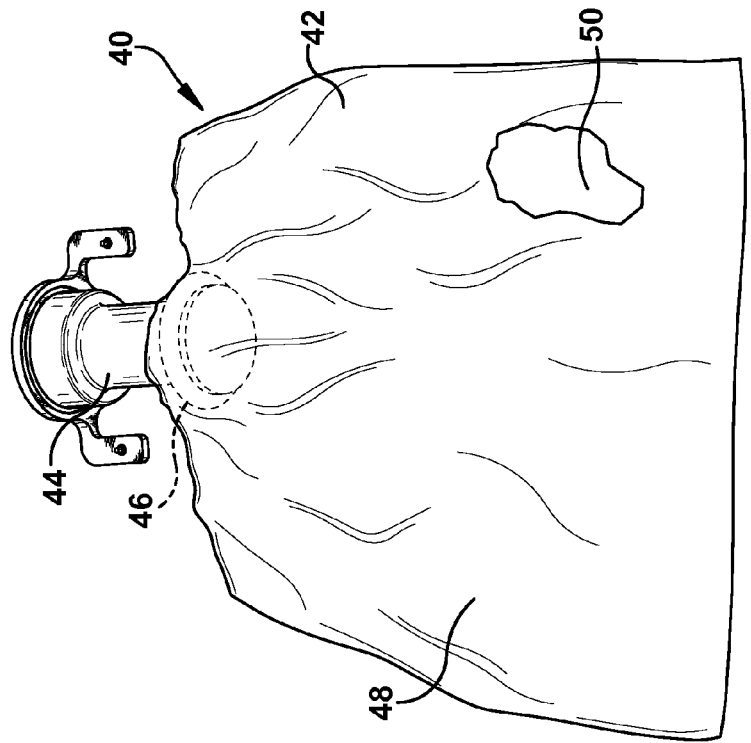
FIG. 3 is a side view of a portion of the container system of FIG. 1, including a bag filled with liquid.

FIGS. 1 and 2 illustrate a medical waste container system 10 for liquid medical waste, in accordance with an example of the present invention. The medical waste container system 10 comprises an outer container 12 that includes an outer container body 14 and an outer container lid 16. The outer container body 14 is a generally rectangular box with four side walls 18, a bottom wall 17, and an open top 19. The open top 19 of the outer container body 14 is covered by the outer container lid 16, which is also generally rectangular in shape. The outer container lid 16 has four side walls 20, a top wall 22, and an open bottom 23. Both the outer container body 14 and the outer container lid 16 are made of relatively rigid plastic, such as High Density Polyethylene (HDPE), which may have a thickness of about three millimeters. The outer container lid 16 is generally transparent. The outer container body 14 may be less transparent than the outer container lid 16 because the plastic of which the outer container body is made may be provided with a conspicuous, highly visible color, such as red. Both the outer container body 14 and the outer container lid 16 may, however, be substantially transparent.

Each side wall 20 of the outer container lid 16 has a horizontal or lateral dimension that is larger than the horizontal or lateral dimension of the corresponding side wall 18 of the outer container body 14. The outer container lid 16 thus overhangs the outer container body 14 when the outer container lid is mounted on the outer container body to close the open top 19 of the outer container body. Two opposed side walls 20 of the outer container lid 16 have horizontal or lateral dimensions that are substantially larger than the horizontal or lateral dimensions of the other two opposed side walls 20 of the outer container lid 16. Handles 32 are formed at opposed ends of the two side walls 20 having substantially larger horizontal or lateral dimensions so as to extend outward of the two side walls 20 having smaller horizontal or lateral dimensions. A latching mechanism 24, which is partially shown schematically in FIGS. 1 and 2, secures the outer container lid 16 on the outer container body 14. The latching mechanism 24 may be any latching mechanism suitable for securing the outer container lid 16 to the outer container body 14. The latching mechanism 24 is releasable so that the outer container lid 16 can be removed from the outer container body 14.

The outer container body 14 and the outer container lid 16 may be any convenient shape provided that the outer container body and the outer container lid, when secured together, provide an enclosed cavity 26. In this regard, the bottom wall 17 of the outer container body is free of any hole or other opening. The top wall 22 of the outer container lid 16, however, has a central opening 28 defined by an annular neck 30 that is formed in one piece with and projects upward from the top wall 22. Medical waste may thus be introduced into the cavity 26 in the outer container 12 through the opening 28.

To receive medical waste introduced into the outer container 12, the medical waste container system 10 also comprises an inner container 40 (FIGS. 4 and 5) that includes a bag 42, a fill tube 44, and an elastic ring 46. The bag 42 includes a flexible body 48 defining an enclosed cavity 50. The flexible body 48 may be formed of any plastic, polymer, or other material that is (a) flexible, (b) impervious to water and other liquids, and (c) strong enough to support a quantity of liquid filling the cavity 50 without rupturing. Suitable materials include Mylar. As used in this application, "flexible" means that a material, such as the material of which the flexible body 48 is made, is capable of being flexed, which is to say capable of being turned, bowed, or twisted without breaking. A fill opening 52 is formed in the flexible body 48 through which medical waste may be introduced into the cavity 50 and thus into the bag 42. Apart from the fill opening 52, the bag 42 is free of any hole or other opening.

Figure 5:
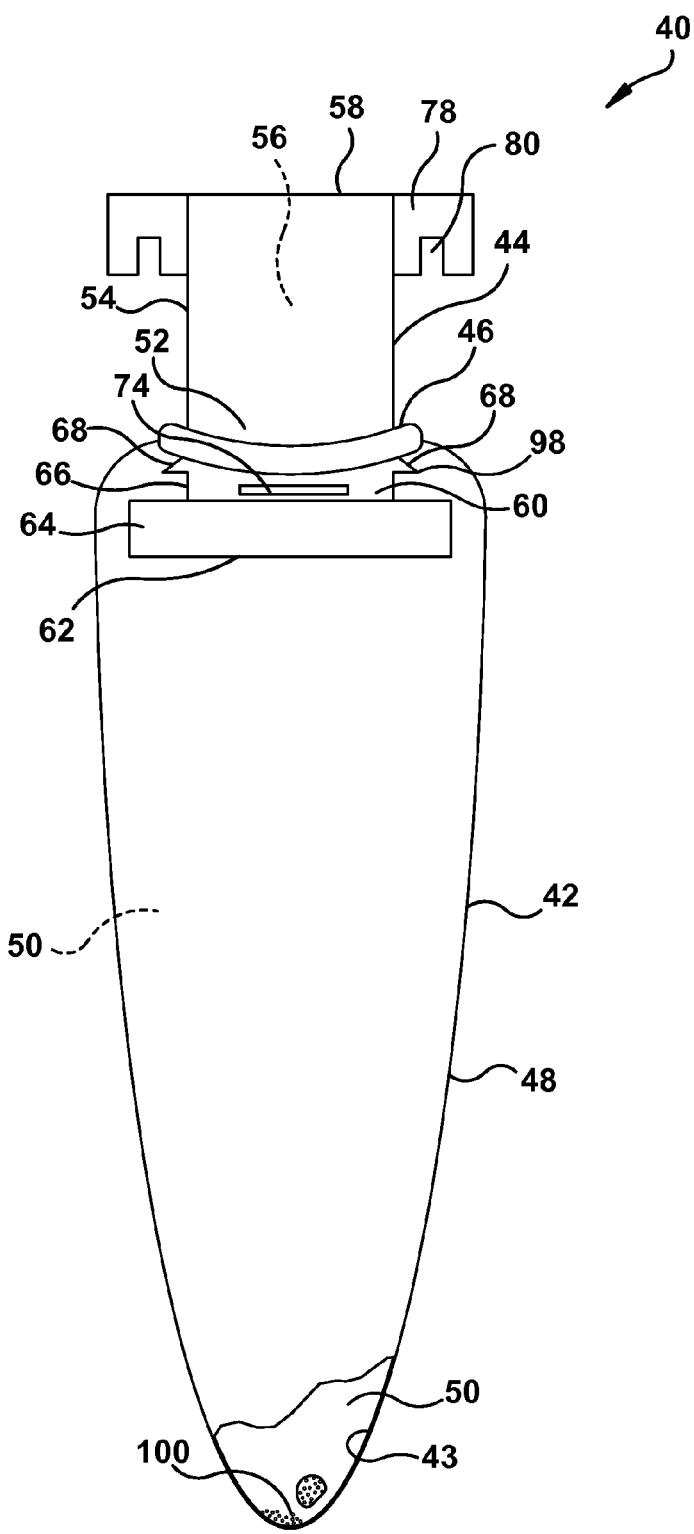
FIG. 5 is a schematic side view of a portion of the container system of FIG. 1.

The fill tube 44 includes a tubular wall 54, which defines a central longitudinal passage 56 that extends lengthwise through the fill tube. The fill tube 44 has an open first end 58 and an opposite closed second end 60. The second end 60 of the fill tube 44 is closed by an end wall 62 that extends entirely across the central longitudinal passage 56. The end wall 62 also extends radially outward from the tubular wall 54 to provide a lip 64 that projects radially outward from an outer surface 66 of the tubular wall all around the circumference of the tubular wall. Either one or both of the end wall 62 and the lip 64 may be at the second end 60 of the tubular wall 54 or may be adjacent to but spaced away from the second end of the tubular wall. The lip 64 and the tubular wall 54 of the fill tube 44 have outer diameters that are smaller than the inner diameter of the neck 30 of the outer container lid 16. Although the end wall 62 is illustrated in FIG. 5, for example, as a disc with exposed, outer major surfaces 63 and 65 that are flat, the portion 67 of the major surface of the end wall 62 that is presented to the central longitudinal passage 56 may have a convex shape. Such a convex shape for the surface of the end wall 62 will facilitate liquid flow, as will become apparent below.

Three tabs 68 also project radially outward from the outer surface 66 of the tubular wall 54. The three tabs 68 are spaced away from the lip 64 in a direction along the length of the tubular wall 54 toward the open first end 58 of the fill tube 44. The three tabs 68 are circumferentially spaced apart from one another around the circumference of the outer surface 66 of the tubular wall 54. Each tab 68 (FIGS. 6B and 8) has a sloped surface 70 and radial surface 72. The sloped surface 70 of each tab 68 intersects the outer surface 66 of the tubular wall 54 and extends at an acute angle away from the outer surface 66 along the length of the tubular wall in a direction toward the closed second end 60 of the fill tube 44. The radial surface 72 of each tab 68 intersects the outer surface 66 of the tubular wall 54 at a location closer to the closed second end 60 of the fill tube 44 than the location at which the sloped surface 70 intersects the outer surface 66 of the tubular wall 54. The radial surface 72 extends radially outward from the outer surface 66 of the tubular wall 54 until it intersects the sloped surface 70 to form a tip or end 98 of the tab 68. Each tab 68 thus slopes gradually away from the outer surface 66 in a direction toward the closed second end 60 of the fill tube 44 and then abruptly turns radially back toward the outer surface 66. The circumferential distance defined by the ends 98 of the tabs 68 and the portions of the tubular wall 54 disposed circumferentially between the tabs is smaller than the outer circumference of the lip 64 for reasons that will be explained below. Although three tabs 68 are shown, a greater or lesser number of tabs may be used.

Along the length of the fill tube 44 between the lip 64 and the tabs 68, multiple discharge openings 74 are formed in the tubular wall 54. The discharge openings 74 extend from an inner surface 76 (FIGS. 6B and 7) of the tubular wall 54 to the outer surface 66 of the tubular wall. The discharge openings 74 communicate with the central longitudinal passage 56 such that liquid in the central longitudinal passage can flow radially outward through the discharge openings to the outer surface 66 of the tubular wall 54. The number and cross-sectional area of the discharge openings 74 may be determined in accordance with the expected volume of liquid to be received in the central longitudinal passage 56 and the expected flow rate needed to prevent the fill tube 44 from overflowing The cross-sectional shape of the discharge openings 74 may vary as needed to promote liquid flow, as can be seen, for example, by comparing the circular cross-section of the discharge openings 74 shown in FIG. 6B with the elongated and flattened cross-section of the discharge opening 74 shown in FIG. 5.

Adjacent the open first end 58 of the fill tube 44, a mounting lip 78 extends radially outwardly from the outer surface 66 of the tubular wall 54. The mounting lip 78 extends radially outward for a distance such that the mounting lip has a larger outer diameter than the neck 30 of the outer container lid 16. The mounting lip 78 is formed with a circular undercut channel 80 that has a diameter equal to the diameter of the neck 30 of the outer container lid 16. When the mounting lip 78 is placed on the neck 30 of the outer container lid 16, therefore, the end of the neck can be received in the undercut channel 80. With such placement of the mounting lip 78, any medical waste introduced into the outer container 12 through the opening 28 must be introduced through the open first end 58 of the fill tube 44 because the mounting lip and the fill tube effectively close off any other access into the cavity 26 in the outer container.

Figure 6A:
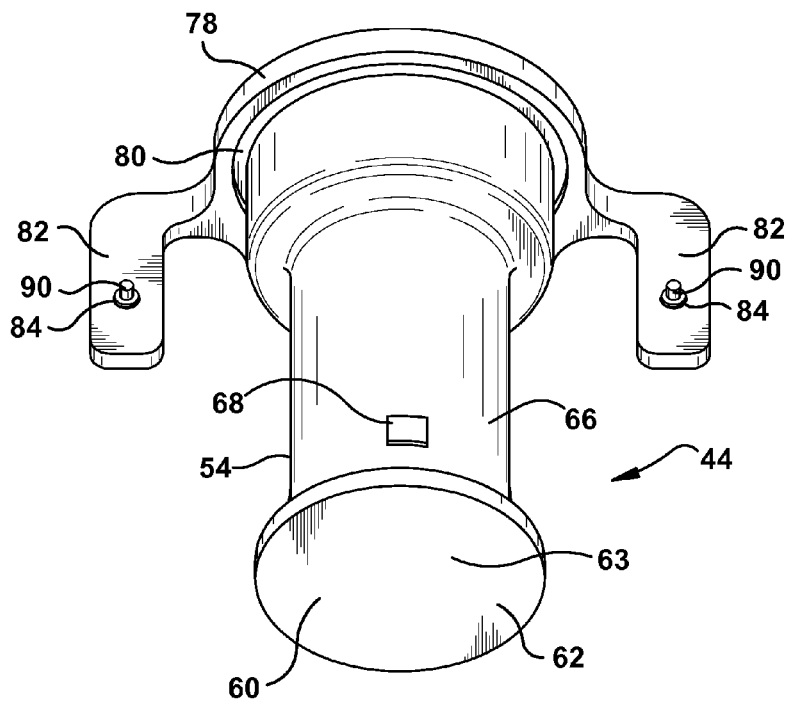
FIG. 6A is a perspective view of a portion of the container system of FIG. 1.
Figure 6B:
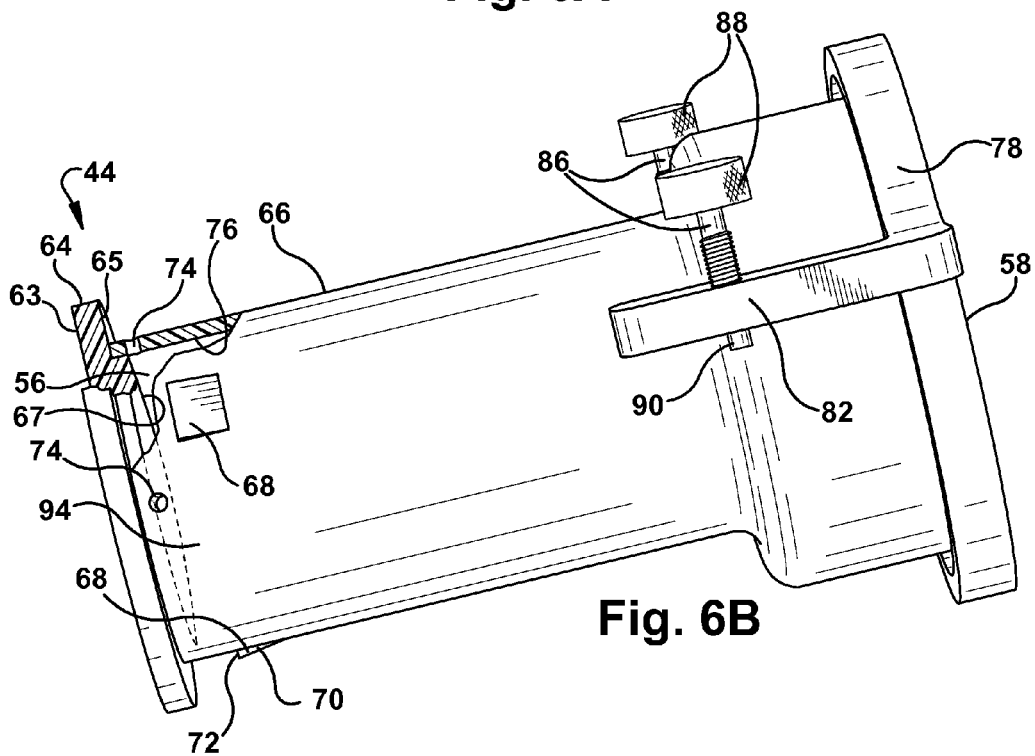
FIG. 6B is a perspective view of the portion of the container system shown in FIG. 6A.
Figure 7:
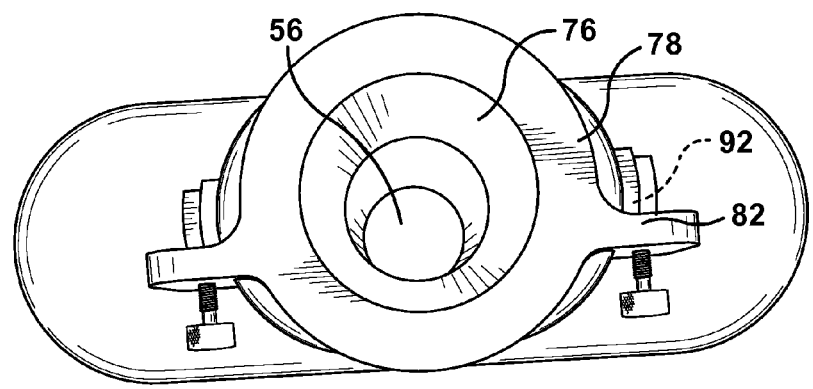
FIG. 7 is a top view of a portion of the container system of FIG. 1.

At two diametrically opposed locations around the outer circumference of the mounting lip 78, an L-shaped lug 82 (FIG. 6A) projects radially outward from the mounting lip and then projects in a direction lengthwise of the fill tube 44 toward the closed second end 60 of the fill tube. As best shown in FIGS. 6A and 6B, a hole 84 is formed in each lug 82 in the portion of the lug that projects in a direction lengthwise of the fill tube 44. A threaded fastener 86 with an enlarged, knurled end 88 is received in each hole 84. The opposite, smaller ends 90 of the threaded fasteners 86 are received in recesses 92 formed in the outer container lid 16, as best shown in FIGS. 2 and 7, to hold the fill tube 44 in place on the neck 30. While the lugs 82, threaded fasteners 86, and recesses 92 together provide one specific embodiment of a mechanism for securing the fill tube 44 to the outer container lid 16, any suitable mechanism for securing the fill tube to the outer container lid may be used. Other configurations of the outer container lid 16, for example, may facilitate or require the use of a different mechanism for securing the fill tube 44 to the outer container lid.

The elastic ring 46 is attached to the flexible body 48 adjacent to and surrounding the fill opening 52. The elastic ring 46 is shaped and dimensioned to encircle and resiliently press against the outer surface 66 of the tubular wall 54 of the fill tube 44. The elastic ring 46 is formed of an elastomeric material, such as an elastomeric foam material. The elastic ring 46 is both flexible and resilient. As used in this application, "resilient" means that a material, such as the material of which the elastic ring 46 is formed, is capable of returning freely to a previous position, shape or condition, which is to say capable of recovering its size and shape after deformation.

To assemble the inner container 40, the closed second end 60 of the fill tube 44 is inserted into the fill opening 52 formed in the flexible body 48 of the bag 42. Inserting the second end 60 of the fill tube 44 into the fill opening 52 requires resiliently expanding or stretching the elastic ring 46 so that the lip 64 at the second end of the fill tube can pass through the elastic ring. Due to the resilience of the material from which the elastic ring 46 is made, the elastic ring will resiliently contract after being expanded or stretched to fit over the lip 64. The fill tube 44 is pushed lengthwise into the flexible body 48 of the bag 42 until the tabs 68 are inside the cavity 50. Because the radial surfaces 72 of the tabs 68 extend radially or perpendicularly outward from the outer surface 66 of the tubular wall 54 of the fill tube 44, the elastic ring 46 will again have to be resiliently expanded or stretched to permit the tabs to pass through the elastic ring and the fill opening 52 of the flexible body 48.

Figure 4:
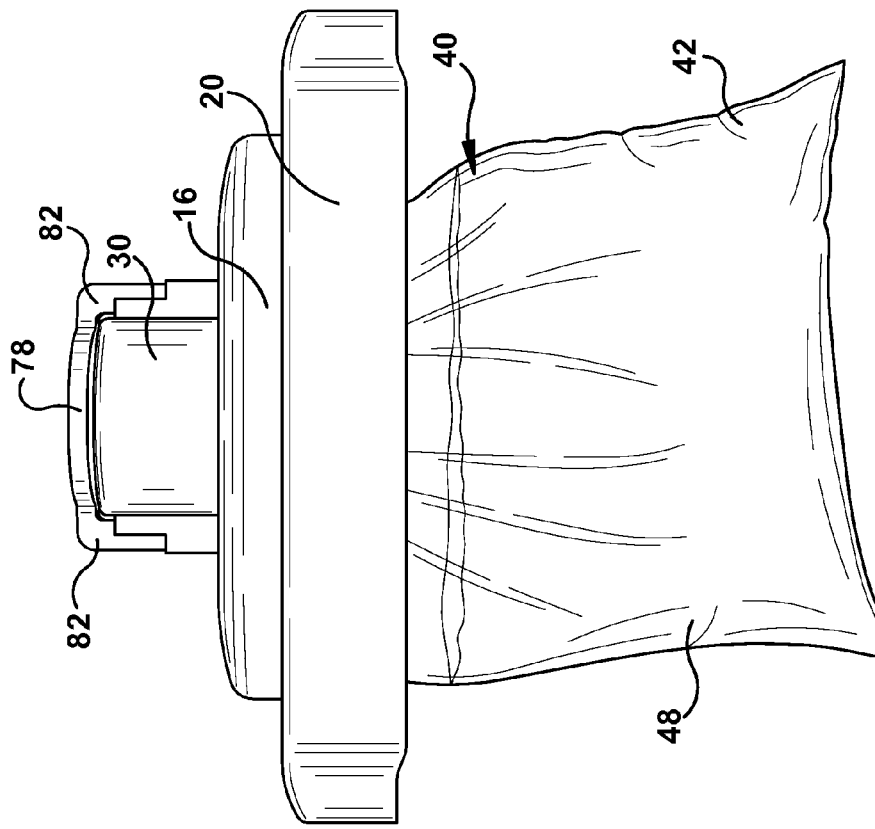
FIG. 4 is a perspective view of the bag of FIG. 3 when empty.

In the final assembled condition of the inner container 40, an end portion 94 of the fill tube 44 is inside the cavity 50 of the bag 42. The end portion 94 of the fill tube 44 includes the lip 64, the tabs 68, and the portion of the tubular wall 54 that extends between the lip and the tabs. The elastic ring 46 encircles and resiliently presses against the outer surface 66 of the tubular wall 54 of the fill tube 44 at a first location or position between the tabs 68 and the open first end 58 of the fill tube. The first location or position of the elastic ring 46 may be immediately adjacent the tabs 68 or may be relatively closer to the open first end 58 of the fill tube. As illustrated in FIGS. 4 and 5, the open first end 58 of the fill tube 44 and a majority of the length of the fill tube project from or out of the fill opening 52 formed in the flexible body 48 of the bag 42.

When assembled as described above, the inner container 40 provides a flow path for liquids that extends from the open first end 58 of the fill tube 44 to the cavity 50 of the bag 42. More specifically, liquid medical waste or other liquid may be introduced into the open first end 58 of the fill tube 44. The liquid will flow from the open first end 58 of the fill tube 44 along the central longitudinal passage 56 of the fill tube to the closed second end 60 of the fill tube. At the closed second end 60 of the fill tube 44, the liquid will flow radially outward through the discharge openings 74 in the tubular wall 54 of the fill tube. As will be apparent, if the surface of the end wall 62 that is presented to the central longitudinal passage 56 has a convex shape, such a convex shape will facilitate liquid flow toward the discharge openings 74. Because the discharge openings 74 are located between the lip 64 and the tabs 68 of the fill tube 44 and because the elastic ring 46 surrounding the fill opening 52 of the bag 42 is initially located closer to the open first end 58 of the fill tube than the tabs, liquid that flows radially outward through the discharge openings will flow into the cavity 50 of the bag. The flow path thus extends from the open first end 58 of the fill tube 44, along the central longitudinal passage 56, through the discharge openings 74, and into the cavity 50 of the bag 42.

The inner container 40 is installed in the outer container 12 by inserting the fill tube 44 into the neck 30 of the outer container lid 16 with the bag 42 passing through the central opening 28 in the top wall 22 of the outer container lid into the cavity 26. Because the outwardly projecting mounting lip 78 adjacent the open first end 58 of the fill tube 44 has an outer diameter that is larger than the outer diameter of the neck 30 of the outer container lid 16, the mounting lip will contact the upper or distal end 31 of the neck to limit the extent to which the fill tube is inserted into the neck. The distal end 31 of the neck 30 is received in the undercut channel 80 in the mounting lip 78 so that the fill tube 44 is supported on the neck of the outer container lid 16. To secure the inner container 40 to the outer container lid 16, the threaded fasteners 86 are screwed into the holes 84 formed in the lugs 82 on the mounting lip 78 so that the smaller ends 90 of the threaded fasteners are received in the recesses 92 in the outer container lid. Installation of the inner container 40 in the outer container 12 may be performed with the outer container lid 16 mounted on the outer container body 14 or removed from the outer container body. As the outer container body 14 may be permanently attached to an immovable structure, such as a wall of a building, removing the outer container lid 16 from the outer container body may be a more convenient manner to install the inner container 40 in the outer container 12. In particular, the inner container 40 may be first installed in the outer container lid 16, and the sub-assembly comprising the inner container and the outer container lid may then be attached to the outer container body 14.

In use, the medical waste container system 10 is provided in a hospital, doctor's office, or other medical facility to receive liquid medical waste, such as excess liquid pharmaceutical compounds. The liquid medical waste is introduced into the medical waste container system 10 through the open first end 58 of the fill tube 44. The liquid medical waste flows downward through the central longitudinal passage 56, radially outward through the discharge openings 74, and into the cavity 50 in the bag 42. As more liquid medical waste is introduced into the bag 42, the weight supported by the bag increases. As the combined weight of the bag 42 and the liquid medical waste in the bag increases, the elastic ring 46 resiliently expands or stretches. At a predetermined combined weight of the bag 42 and the liquid medical waste in the bag, the elastic ring 46 will have expanded or stretched sufficiently that the elastic ring will have slipped down the sloped surfaces 70 of the tabs 68 and over the ends 98 of the tabs defined by the intersections of the sloped surfaces with the radial surfaces 72. Because the tubular wall 54 of the fill tube 44 has a smaller outer circumference than the circumferential distance defined by the ends 98 of the tabs 68 and the portions of the tubular wall disposed circumferentially between the tabs, the elastic ring 46 will resiliently contract into contact with the outer surface 66 of the tubular wall after passing over the tabs and will also slide down the outer surface of the tubular wall under the load imposed by the combined weight of the bag 42 and the liquid medical waste in the bag.

When the elastic ring 46 slides sufficiently far down the outer surface 66 of the tubular wall 54 of the fill tube 44, the elastic ring contacts the radially extending lip 64. Because the lip 64 projects radially outward from the tubular wall 54 and has a larger outer circumference than the circumferential distance defined by the ends 98 of the tabs 68 and because the surface 65 of the lip is flat and not sloped to facilitate stretching of the elastic ring 46, the combined weight of the bag 42 and the liquid medical waste in the bag is not sufficient to cause the elastic ring 46 to expand resiliently or stretch to the extent necessary to pass over the lip. Instead, the elastic ring 46 continues to press resiliently against the outer surface 66 of the tubular wall 54 in a location or position adjacent the lip 64. In the foregoing location or position, the elastic ring 46 blocks the radially outermost ends of the discharge openings 74 and thus blocks the flow path into the bag 42. No additional liquid may thereafter be introduced into the cavity 50 in the bag 42. The inner container 40 may then be removed from the outer container 12 and replaced with a different inner container or at least the bag 42 and elastic ring 46 may be replaced with a different bag and elastic ring.

Although the bag 42 of the inner container 40 can receive and hold liquid medical waste in its original liquid form, storage of medical waste in the bag can be facilitated, and potential diversion of the medical waste can be made more difficult, by placing an absorbent material 100 in the bag. The absorbent material 100 may comprise only a liquid absorbing material or may comprise a liquid absorbing material in combination with other materials. For example, the liquid absorbing material may be a superabsorbent polymer, which may be formed from polymerization of acrylic acid blended with sodium hydroxide in the presence of an initiator to form a poly-acrylic acid sodium salt, also known as sodium poly acrylate. Another material that may be included in the absorbent material 100 may be a liquid detergent, such as sodium dodecyl sulfate. Such detergents facilitate absorption of water from lipid-emulsion medications, help render the liquid waste in the bag 42 unpalatable, and may add a pleasant fragrance to the liquid waste in the bag. Yet another material that may be included in the absorbent material 100 may be polyethylene glycol 3350, which also facilitates absorption of liquids and helps render the liquid medical waste unusable for purposes intended by unauthorized diversion of such liquid medical waste. Still another material that may be included in the absorbent material 100 may be a dye, such as a food dye, which may also help render the liquid waste in the bag 42 unpalatable and may facilitate visual determination of whether the bag is full. A further material that may be included in the absorbent material 100 may be an oxidizing agent. The absorbent material 100 may be in any suitable physical form, such as a powder or pellets. The absorbent material 100 may also be placed in either a loose or a compacted form in the bag 42 and/or may be applied to an inner surface 43 of the bag 42.

Determining whether the bag 42 of the inner container 40 is filled may be accomplished by visual inspection. Even though the elastic ring 46 of the inner container 40 will function to prevent additional liquid medical waste from being introduced into the bag 42 when the bag is filled, such medical waste may continue to be introduced into the fill tube 44 until a visual inspection determines that the bag is filled and a replacement bag or inner container 40 is substituted. To prevent liquid medical waste from being introduced into the fill tube 44 after the bag 42 is filled, a closure assembly may be added to the inner container 40 to close the open first end 58 of the fill tube. The closure assembly may be any closure assembly that will close the open first end 58 of the fill tube 44 when the bag 42 is filled, but one particular embodiment of such a closure assembly is illustrated in FIG. 8.

Figure 8:
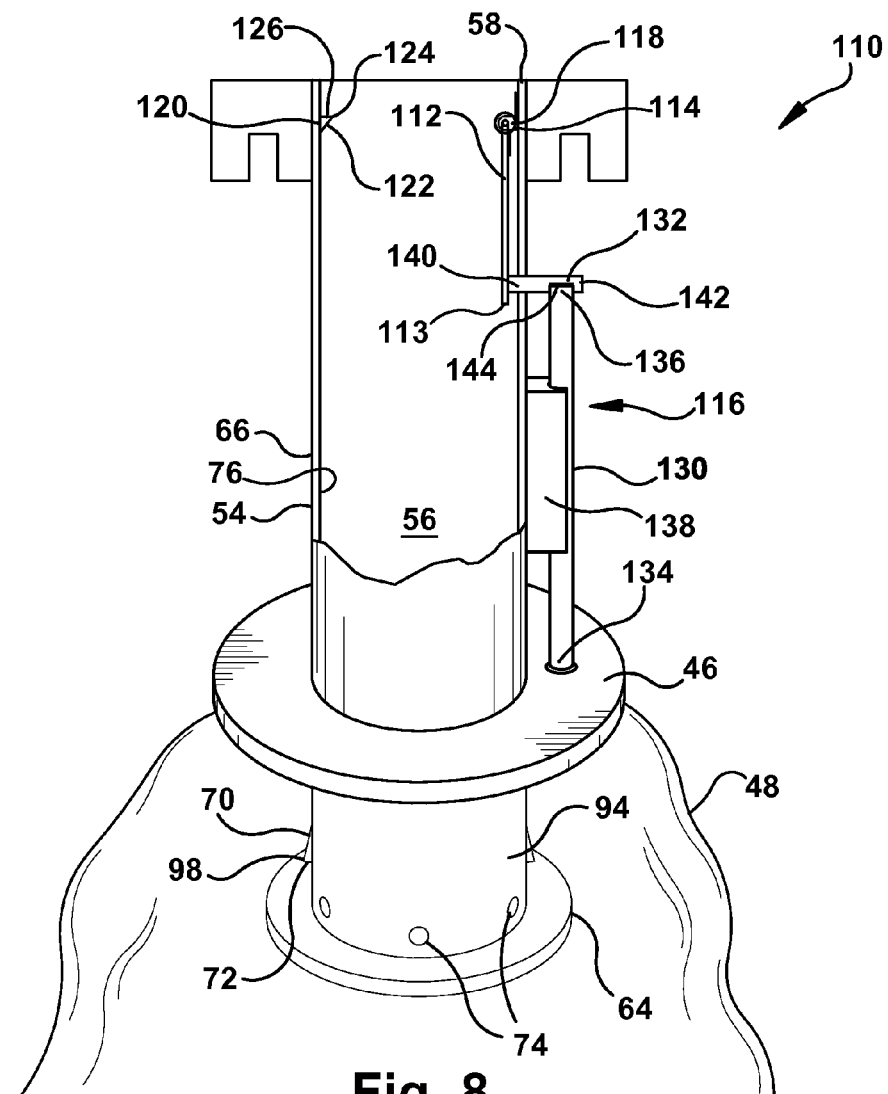
FIG. 8 is a schematic side view of a portion of a modified container system in accordance with the present invention.

As shown schematically in FIG. 8, a closure assembly 110 may include a closure flap 112, a spring 114, and a releasable coupling 116. For purposes of illustrating the closure assembly 110, the portion of the fill tube 44 adjacent the closure assembly is shown as being longer than it would actually be. The closure flap 112 is mounted on the tubular wall 54 of the fill tube 44 at the open first end 58 of the fill tube. The closure flap 112 is connected to the tubular wall 54 by a hinge 118. The hinge 118 may be located on the inner surface 76 of the tubular wall 54, as shown, or on the outer surface 66 of the tubular wall or on the mounting lip 78. The spring 114 may be wrapped around the hinge 118 or otherwise coupled to the closure flap 112 so as to bias or press the closure flap 112 into a closed position covering or blocking the open first end 58 of the fill tube 44. In FIG. 8, the closure flap 112 is located inside the fill tube 44 and in the central longitudinal passage 56. Consequently, the spring 114 biases the closure flap 112 to pivot in an upward direction around the hinge 118 or, as viewed in FIG. 8, in a clockwise direction.

A locking tab 120 projects radially inward from the inner surface 76 of the tubular wall 54. The locking tab 120 has the same shape as the tabs 68 on the outer surface 66 of the tubular wall 54, but is inverted in its orientation as compared to the tabs 68. A sloped surface 122 of the locking tab 120 thus facilitates closing of the closure flap 112 by allowing an edge or edge surface 113 of the closure flap to slide along the sloped surface under the bias of the spring 114. Such sliding motion of the closure flap 112 may be facilitated by resilient flexing of the closure flap, the tubular wall 54, and/or the locking tab 120. Once the closure flap 112 passes upward beyond the tip or end 124 of the locking tab 120, the resilient flexing of the closure flap, the tubular wall 54, and/or the locking tab may help cause the closure flap to move into a position above the radial surface 126 of the locking tab 120 so that interference between the closure flap and the radial surface will hold the closure flap in its closed position. A further structure may be required to hold the closure flap 112 against further upward movement beyond the radial surface 126 of the locking tab 120. Such further structure may be attached to the tubular wall 54, the mounting lip 78 or the hinge 118.

The releasable coupling 116 holds the closure flap 112 in its open position and releases the closure flap to move to its closed position under the bias of the spring 114. As shown schematically in FIG. 8, the releasable coupling 116 includes a rod 130 and notched arm 132. The rod 130 extends along the length of and is substantially parallel to the fill tube 44. At its lower end 134, the rod 130 is attached to the elastic ring 46 so as to move with the elastic ring as the elastic ring slides downward along the fill tube 44. At its opposite upper end 136, the rod 130 engages the notched arm 132. Intermediate its lower and upper ends 134 and 136, the rod 130 passes through an alignment groove in a raised track 138 that projects radially outward from the outer surface 66 of the tubular wall 54 and that extends along the length of the tubular wall. The alignment groove in the raised track 138 helps to maintain the rod 130 in its desired orientation.

The notched arm 132 is attached at its inner end 140 to the closure flap 112. Adjacent its opposite outer end 142, the notched arm 132 has a downward facing notch 144. Between its inner and outer ends 140 and 142, the notched arm 132 passes through an opening (not shown) in the tubular wall 54. The notch 144 in the notched arm 132 engages the upper end 136 of the rod 130 when the elastic ring 46 is in its first location or position between the tabs 68 and the open first end 58 of the fill tube. Engagement between the upper end 136 of the rod 130 and the notch 144 of the notched arm 132 maintains the closure flap 112 in its open position. When the elastic ring 46 slips over the tabs 68 and into its second location or position between the tabs 68 and the lip 64, the lower end 134 of the rod 130 is pulled downward by the movement of the elastic ring, and the upper end 136 of the rod is pulled out of engagement with the notch 144. The closure flap 112 is then free to move to its closed position under the bias of the spring 114 to block the open first end 58 of the fill tube 44.

In the illustrated medical waste container system 10, the inner container 40 is first assembled from the bag 42, fill tube 44, and elastic ring 46 and then installed in the outer container 12. Potentially, however, the fill tube 44 could be first attached to the outer container lid 16 and then the bag 42 with the attached elastic ring 46 could be placed over the closed second end 60 of the fill tube to complete the inner container 40. The fill tube 44 might also be permanently attached to the outer container lid 16, such as by being molded in one piece with or laser welded to the outer container lid. With such an attachment of the fill tube 44 to the outer container lid 16, installation of the inner container 40 in the outer container 12 would require removing the outer container lid from the outer container body 14 before assembling the inner container.

Although the medical waste container system 10 is intended primarily for liquid medical waste, it may be desirable to use the medical waste container system to receive certain other medical waste, such as solid pharmaceutical compositions in pill or capsule form and transdermal patches containing pharmaceutical compositions. Because such solid pharmaceutical compositions and transdermal patches are not in liquid form, they need to be handled somewhat differently than liquid medical waste and should be converted to a physical form that can be more readily treated chemically and received in the medical waste container system.

Figure 9:
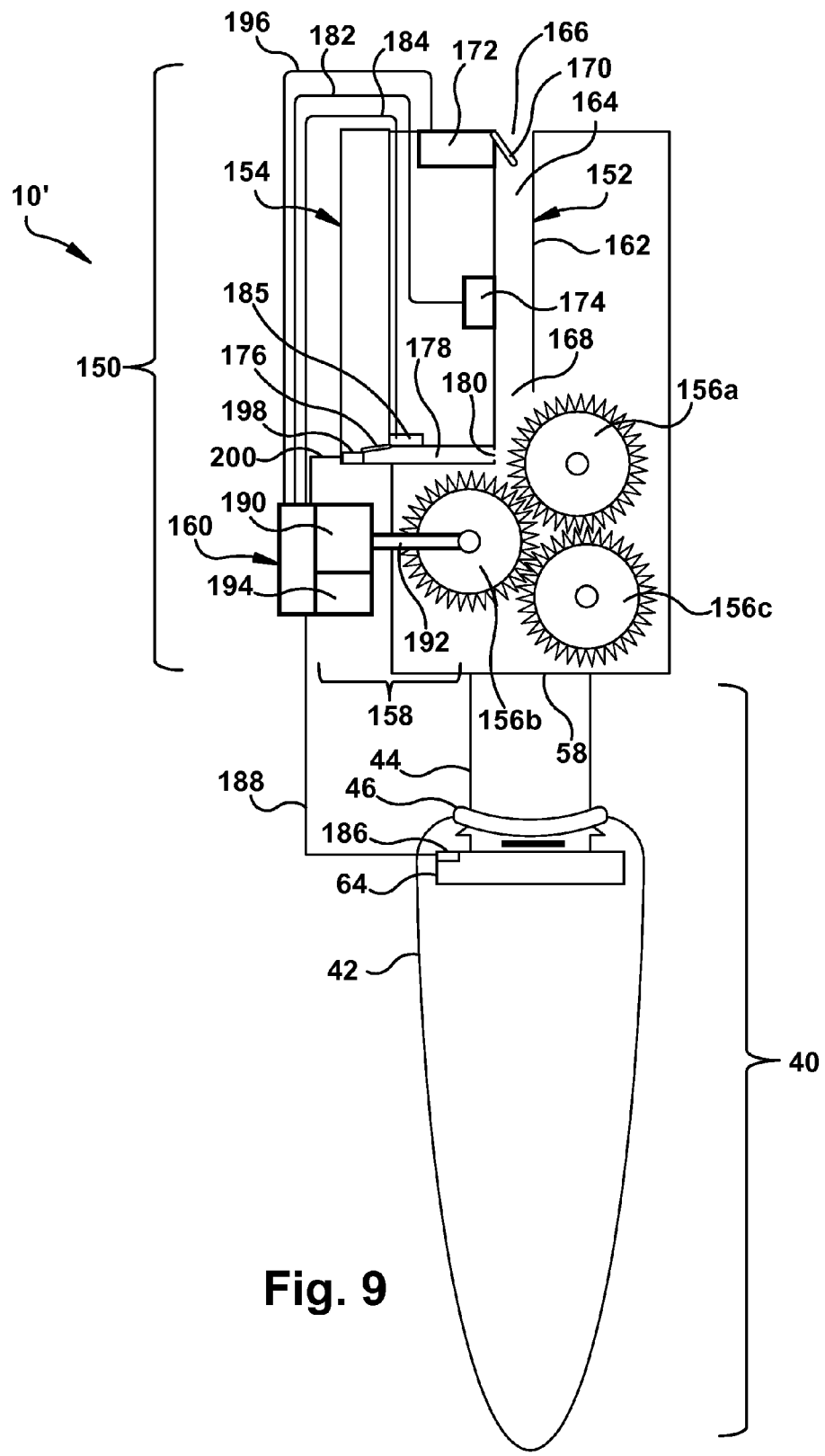
FIG. 9 is a schematic side view of another modified container system in accordance with the present invention.

FIG. 9 schematically illustrates a solid waste processing assembly 150, which can be combined with, for example, the inner container 40 of the medical waste container system 10 to form a modified medical waste container system 10'. As shown, the solid waste processing assembly 150 is mounted above an inner container 40 and, more specifically, above the open first end 58 of the fill tube 44 for the inner container. Although the solid waste processing assembly 150 is shown as having a width or lateral dimension that is about twice as large as diameter or width of the fill tube 44, the widths of the solid waste processing assembly and the fill tube may be more nearly equal to one another or more disparate.

The solid waste processing assembly 150 comprises (a) an inlet chute 152, (b) a fluid reservoir 154 to receive a liquid agent for chemically neutralizing or destroying pharmaceutical compositions, (c) a set of cutting and grinding cylinders or wheels 156a, 156b, and 156c, (d) a drive subassembly 158 to effect operation of the cutting and grinding wheels, and (e) a processor or controller 160. Within the solid waste processing assembly 150, the inlet chute 152 is disposed above the cutting and grinding wheels 156 *a-c*. The inlet chute 152 includes a tubular wall 162. The tubular wall 162 defines a central longitudinal passage 164 that extends lengthwise through the inlet chute. The inlet chute 152 has an open first end 166 and an opposite open second end 168. The open first end 166 provides the entrance to the inlet chute 152. The entrance to the inlet chute 152 may be just large enough to accommodate large pills or capsules and/or folded transdermal patches. The open first end 166 may be closed by a closure flap 170. The closure flap 170 may normally be in an open position to facilitate placing medical waste in the solid waste processing assembly 150. A closure actuator 172, which may be electrically operated, may be used to cause the closure flap 170 to assume a closed position across and blocking the open first end 166 of the inlet chute 152.

The open second end 168 of the inlet chute 152 is positioned adjacent to and above or vertically higher than the cutting and grinding wheels 156*a-c*. Medical waste introduced into the open first end 166 of the inlet chute 152 thus will fall through the central longitudinal passage 164 and out of the inlet chute onto the cutting and grinding wheels 156*a-c*. Between the open first end 166 and the open second end 168 of the inlet chute 152, an activation sensor 174 is mounted in or adjacent to the tubular wall 162 of the inlet chute. The activation sensor 174, which may be, for example, an ultrasonic, microwave, or passive infrared sensor, detects or senses when material passes through the central longitudinal passage 164. Such material may be entirely solid medical waste, but may also include or may alternatively be liquid medical waste. The activation sensor 174 then provides a signal indicative of the passing of such material. The signal provided by the activation sensor 174 is used to activate the cutting and grinding wheels 156*a-c* and to activate an outlet valve 176 for the fluid reservoir 154, as will be explained in more detail below.

The fluid reservoir 154 receives a liquid agent for chemically neutralizing or destroying pharmaceutical compositions. Suitable liquid agents include an aqueous solution of calcium hypochlorite or an aqueous solution of sodium hypochlorite. The outlet valve 176 for the fluid reservoir 154 is located at or near the bottom of the fluid reservoir. The outlet valve 176 controls fluid flow out of the fluid reservoir 154 into a short outlet tube or passage 178. An end 180 of the outlet passage 178 spaced away from the outlet valve 176 and the fluid reservoir 154 is both open and disposed at a location above or vertically higher than at least some of the cutting and grinding wheels 156*a-c*. Consequently, when the outlet valve 176 is open, liquid from the reservoir will flow through the outlet passage 178 onto at least some of the cutting and grinding wheels 156*a-c* and onto any solid waste material being pulverized and/or shredded by the cutting and grinding wheels. The liquid, which contains the agent for chemically neutralizing or destroying pharmaceutical compositions in the solid waste material, intimately contacts and mixes with the pharmaceutical compositions in the solid waste due to the pulverized and/or shredded condition of the solid waste material and the rotary movement of the cutting and grinding wheels 156*a-c*.

Activation of the cutting and grinding wheels 156*a-c* and the outlet valve 176 for the fluid reservoir 154 in response to the signal provided by the activation sensor 174 is effected through the controller 160. More specifically, the activation sensor 174 is connected through an electrical line 182 to the controller 160. The controller 160, in turn, is connected through an electrical line 184 to an actuator 185 for the outlet valve 176. Upon receipt of the signal from the activation sensor 174 through the electrical line 182, the controller 160 checks whether the inner container 40 is full. To permit the controller 160 to determine whether the inner container 40 is full, a "bag full" sensor 186 is mounted in or adjacent to the inner container. As shown in FIG. 9, the "bag full" sensor 186 is a pressure sensor mounted on the lip 64 of the fill tube 44 of the inner container 40. When the elastic ring 46 of the inner container 40 contacts the lip 64 due to the weight of the bag 42 and the medical waste in the bag, the pressure applied by the elastic ring to the "bag full" sensor 186 will cause a signal to be delivered to the controller 160 through an electrical line 188 electrically connecting the controller and the "bag full" sensor. The "bag full" sensor 186 may be any type of sensor capable of detecting whether and when the bag 42 is full. For example, the "bag full" sensor 186 may be an optical sensor that is adhered to the outside of the bag 42 or adhered to the inside of an outer container and that is set to send a signal when the material in the bag reaches a predetermined "bag full" level or line.

If the controller 160 receives a signal from the activation sensor 174 and also determines from the "bag full" sensor 186 that the bag 42 of the inner container 40 is not full, the controller sends a signal through the electrical line 184 to the actuator 185 for the outlet valve 176 to open the outlet valve and permit fluid to flow from the fluid reservoir. The actuator may, for example, open the outlet valve 176 for a predetermined length of time. At the same time, the controller 160 sends a signal to the drive subassembly 158 to actuate the drive subassembly. The drive subassembly 158 may include an electric motor 190 and a shaft assembly 192. The electric motor 190 rotates the shaft assembly 192 to cause the cutting and grinding wheels 156*a-c* to be rotated and thereby cut, shred, pulverize or otherwise reduce in size the solid waste material. As shown in FIG. 9, the controller 160 is mounted on the electric motor 190 and a power supply 194, such as a battery, for the electric motor and, potentially, for the entire solid waste processing assembly 150. The controller 160 could, however, be spaced away from the electric motor 190 and/or the power supply 194.

If the controller 160 determines from the "bag full" sensor 186 that the bag 42 of the inner container 40 is full, the controller will not send a signal to the outlet valve 176 to open the outlet valve or send a signal to the electric motor 190 to actuate the electric motor. Moreover, if the controller 160 determines from the "bag full" sensor 186 that the bag 42 of the inner container 40 is full, the controller will send a signal through an electrical line 196 to the closure actuator 172 to close the closure flap 170 to ensure that additional medical waste is not introduced into the solid waste processing assembly 150. The controller 160 may also actuate a "bag full" light or other indicator (not shown). If the controller 160 determines from the "bag full" sensor 186 that the bag 42 is full while the solid waste processing assembly 150 is operating, the controller will send a signal to close the outlet valve 176 and a signal to stop the electric motor so that no additional liquid from the fluid reservoir 154 and no additional solid waste from the cutting and grinding wheels 156*a-c* will be introduced into the fill tube 44 of the inner container 40.

To help further ensure that solid medical waste introduced into the solid waste processing assembly 150 is fully processed, a liquid level sensor 198 may be mounted in the fluid reservoir 154 at or near the bottom of the fluid reservoir. If the liquid level sensor 198 determines that the fluid reservoir is empty, the liquid level sensor 198 sends a signal through an electrical line 200 to the controller 160. Upon receipt of a signal from the liquid level sensor 198, the controller 160 sends a signal to the closure actuator 172 to close the closure flap 170 to ensure that additional medical waste is not introduced into the solid waste processing assembly 150. As an additional feature, the fluid reservoir 154 may have a volume capacity that is less than the volume capacity of the bag 42 so that the liquid level sensor 198 will send a "reservoir empty" signal to the controller 160 and the controller 160 will send a signal to the closure actuator 172 to block the introduction of additional medical waste before the bag 42 is completely full. Still further, the bag 42 may be provided with a small initial quantity of a neutralizing agent or oxidizing agent in liquid or tablet form to neutralize solid or liquid medical waste that, for example, may be in the solid waste processing assembly 150 but not fully processed when the fluid reservoir 154 has discharged all of its neutralizing agent.

As indicated in the foregoing description, the solid waste processing assembly 150 effectively comprises (a) a reducing mechanism operable to reduce solid waste material to a smaller reduced size and (b) a neutralizing mechanism operable to treat the solid waste material with a liquid neutralizing agent to neutralize pharmaceutical products in the solid waste material. The reducing mechanism includes the cutting and grinding cylinders or wheels 156a, 156b, and 156c and the drive subassembly 158. The neutralizing mechanism includes the fluid reservoir 154, the outlet valve 176, and the actuator 185 for the outlet valve.

The solid waste processing assembly 150 may be constructed with all of its components, such as the inlet chute 152, the fluid reservoir 154, the cutting and grinding wheels 156a, 156b, and 156c, the drive subassembly 158, and the processor or controller 160, connected together as an integrated structural unit that may be handled, installed, and moved without having to handle separately any of the components. Alternatively, the solid waste processing assembly 150 may be constructed with one or more components operatively coupled to other components and/or structurally connected with the other components in a manner that facilitates handling or moving certain components as a unit, while leaving other components in place, for example, on a building wall or other support. Also, although the processor or controller 160 of the solid waste processing assembly in the modified medical waste container system 10' may be connected to the sensors and actuators by electrical wires, as shown in FIG. 9, for transmission of various electrical signals, such signals may also be transmitted and received wirelessly. Further, the power supply for the drive subassembly 158 and/or the entire solid waste processing assembly 150 may be a plug or other connection to a supply line for electricity from an external power supply or grid, rather than a battery.

As will be appreciated, using the inner container 40 in combination with the solid waste processing assembly 150 in the modified medical waste container system 10' may require some modification of the inner container 40 shown in FIGS. 5-7. For example, the discharge openings 74 in the tubular wall 54 of the fill tube 44 may need to be larger in size in order to accommodate solid waste material, even if the solid waste material is reduced in size by the solid waste processing assembly 150. Nonetheless, the modified medical waste container system 10' would still be capable of receiving liquid medical waste like the medical waste container system 10. In addition, while the modified medical waste container system 10' is shown in FIG. 9 as incorporating the inner container 40, the modified medical waste container system 10' could also include an outer container similar to the outer container 12 of FIGS. 1 and 2.

From the above description of the invention, those skilled in the art will perceive improvements, changes and modifications. Such improvements, changes, and/or modifications within the skill of the art are intended to be covered by the appended claims.

Having described the invention, the following is claimed:

1. A container for collecting liquid medical waste comprising:
    a bag including a flexible body defining a cavity in the bag, the bag also including a fill opening formed in the flexible body;
    a fill tube including a tubular wall, the fill tube having an open first end and an opposite closed second end, the tubular wall including an inner circumferential surface extending lengthwise of the tubular wall and an outer circumferential surface extending lengthwise of the tubular wall, the inner circumferential surface defining a longitudinal passage extending from the first end of the fill tube toward the second end, the fill tube also including a wall extending across the longitudinal passage to close the second end of the fill tube, the second end of the fill tube being receivable in the cavity of the bag with the first end of the fill tube being disposed outside of the cavity and at least a portion of a length of the tubular wall projecting through the fill opening in the flexible body; and
    an elastic ring directly attached to the flexible body adjacent to and surrounding the fill opening, the elastic ring being shaped and dimensioned to encircle and resiliently press against the outer circumferential surface of the tubular wall of the fill tube,
    the fill tube further including (a) a lip projecting radially outward from the outer circumferential surface of the tubular wall adjacent the second end of the fill tube, (b) a tab on and projecting radially outward from the outer circumferential surface of the tubular wall at a location spaced apart from the lip in a direction along the tubular wall toward the first end, and (c) a discharge opening formed in the tubular wall of the fill tube between the lip and the tab, the discharge opening extending radially outward through the tubular wall from the inner circumferential surface of the tubular wall to the outer circumferential surface of the tubular wall and communicating with the longitudinal passage,
    a flow path for liquids extending from the open end of the fill tube through the longitudinal passage and the discharge opening into the cavity when the cavity receives the second end of the fill tube and the lip such that the elastic ring encircles the outer circumferential surface of the fill tube at a first position between the tab and the first end of the fill tube, the flow path being blocked when the elastic ring encircles the outer circumferential surface of the fill tube at a second position between the lip and the tab in which the elastic ring extends across and blocks a radially outer end of the discharge opening, the tab being shaped and dimensioned and the elastic ring being formed such that the elastic ring resiliently expands to slip over the tab from the first position to the second position in response to increased weight of the bap resulting from liquid flowing through the flow path into the cavity and adding weight to the bag.

2. A container according to claim 1 further comprising an absorbent material in the cavity of the bag.

3. A container according to claim 1, wherein the lip is shaped and dimensioned and the elastic ring is formed to prevent the elastic ring from resiliently expanding to slip over the lip from the second position in response to liquid flowing through the flow path into the cavity and adding weight to the bag.

4. A container according to claim 1 further comprising an outer body in which the bag is received.

5. A container according to claim 4 further comprising a lid for the outer body, the first end of the fill tube projecting out of the outer body through the lid.

6. A system for collecting medical waste comprising:
a solid waste processing assembly, the solid waste processing assembly including (a) a reducing mechanism including relatively movable mechanical elements and operable to cause relative movement of the relatively movable mechanical elements so as to reduce mechanically items of solid waste material from a first size to a second smaller reduced size and (b) a neutralizing mechanism operable to treat the solid waste material with a flow of a liquid neutralizing agent to neutralize pharmaceutical products in the solid waste material;
a bag including a flexible body defining a cavity in the bag, the bag also including a fill opening formed in the flexible body;
a fill tube including a tubular wall, the fill tube having an open first end and an opposite closed second end, the tubular wall including an inner circumferential surface extending lengthwise of the tubular wall and an outer circumferential surface extending lengthwise of the tubular wall, the inner circumferential surface defining a longitudinal passage extending from the first end of the fill tube toward the second end, the fill tube also including a wall extending across the longitudinal passage to close the second end of the fill tube, the second end of the fill tube being receivable in the cavity of the bag with the first end of the fill tube being disposed outside of the cavity and at least a portion of a length of the tubular wall projecting through the fill opening in the flexible body, the first end of the fill tube being in communication with the solid waste processing assembly; and
an elastic ring directly attached to the flexible body adjacent to and surrounding the fill opening, the elastic ring being shaped and dimensioned to encircle and resiliently press against the outer circumferential surface of the tubular wall of the fill tube,
the fill tube further including (i) a lip projecting radially outward from the outer circumferential surface of the tubular wall adjacent the second end of the fill tube, (ii) a tab on and projecting radially outward from the outer circumferential surface of the tubular wall at a location spaced apart from the lip in a direction along the tubular wall toward the first end, and (iii) a discharge opening formed in the tubular wall of the fill tube between the lip and the tab, the discharge opening extending radially outward through the tubular wall from the inner circumferential surface of the tubular wall to the outer circumferential surface of the tubular wall and communicating with the longitudinal passage,
a flow path for liquids and for reduced size solid waste material extending from the open end of the fill tube through the longitudinal passage and the discharge opening into the cavity when the cavity receives the second end of the fill tube and the lip such that the elastic ring encircles the outer circumferential surface of the fill tube at a first position between the tab and the first end of the fill tube, the flow path being blocked when the elastic ring encircles the outer circumferential surface of the fill tube at a second position between the lip and the tab in which the elastic ring extends across and blocks a radially outer end of the discharge opening, the tab being shaped and dimensioned and the elastic ring being formed such that the elastic ring resiliently expands to slip over the tab from the first position to the second position in response to increased weight of the bag resulting from liquid and reduced size solid waste material passing through the flow path into the cavity and adding weight to the bag.

7. A system according to claim 6 further comprising an absorbent material in the cavity of the bag.

8. A system according to claim 6, wherein the lip is shaped and dimensioned and the elastic ring is formed to prevent the elastic ring from resiliently expanding to slip over the lip from the second position in response to liquid and reduced size solid waste material passing through the flow path into the cavity and adding weight to the bag.

* * * * *

UNITED STATES PATENT AND TRADEMARK OFFICE
CERTIFICATE OF CORRECTION

PATENT NO. : 9,707,324 B2
APPLICATION NO. : 14/681515
DATED : July 18, 2017
INVENTOR(S) : Joseph W. Morgan et al.

Page 1 of 1

It is certified that error appears in the above-identified patent and that said Letters Patent is hereby corrected as shown below:

Column 16, Line 62 reads "bap" should read --bag--

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*